(12) United States Patent
Gracias et al.

(10) Patent No.: US 7,795,248 B2
(45) Date of Patent: Sep. 14, 2010

(54) SUBSTITUTED 7,8-DIHYDRO-1H-PYRIMIDO[4,5-B][1,4] DIAZEPIN-4-AMINES ARE NOVEL KINASE INHIBITORS

(75) Inventors: Vijaya J. Gracias, Lindenhurst, IL (US); Celerino Abad-Zapatero, Lake Forest, IL (US); Stevan W. Djuric, Libertyville, IL (US); Zhiqin Ji, Libertyville, IL (US); Michael R. Michaelides, Libertyville, IL (US); Kent D. Stewart, Gurnee, IL (US); Irini Zanze, Libertyville, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 793 days.

(21) Appl. No.: 11/432,931

(22) Filed: May 12, 2006

(65) Prior Publication Data

US 2006/0270663 A1 Nov. 30, 2006

Related U.S. Application Data

(60) Provisional application No. 60/682,290, filed on May 18, 2005.

(51) Int. Cl.
*A61K 31/55* (2006.01)
*C07D 487/00* (2006.01)
*A61P 37/00* (2006.01)
*A61P 35/04* (2006.01)

(52) U.S. Cl. ........................ 514/221; 540/568
(58) Field of Classification Search .............. 514/221; 540/568
See application file for complete search history.

(56) References Cited

FOREIGN PATENT DOCUMENTS

| WO | 97/42187 | 11/1997 |
|---|---|---|
| WO | 0119828 | 3/2001 |
| WO | 2004056830 | 7/2004 |

OTHER PUBLICATIONS

Saitz, C. et al., Reaction of 4,5,6-Triaminopyrimidine and 2,4,5,6-Tetraaminopyrimidine wit 3-Dimethylaminopropiophenones. Synthesis of New 4-Aryl-2,3-dihydropyrimido[4,5-b][1,4]diazepines, J. Heterocyclic Chem. 2000, 401-403, vol. 37.
PCTUS2006018796 Search Report, Feb. 15, 2007.

*Primary Examiner*—Brenda L Coleman
(74) *Attorney, Agent, or Firm*—Patricia Coleman-James

(57) ABSTRACT

Compounds having the Formula (I)

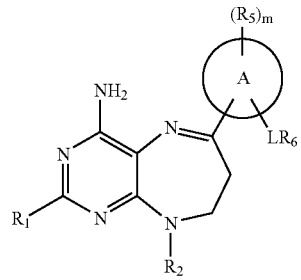

are useful for inhibiting protein tyrosine kinases. The present invention also discloses methods of making the compounds, compositions containing the compounds, and methods of treatment using the compounds.

7 Claims, No Drawings

SUBSTITUTED 7,8-DIHYDRO-1H-PYRIMIDO[4,5-B][1,4] DIAZEPIN-4-AMINES ARE NOVEL KINASE INHIBITORS

This application claims priority from U.S. Provisional Patent Application No. 60/682,290, filed May 18, 2005.

TECHNICAL FIELD

The present invention relates to novel substituted 7,8-dihydro-1H-pyrimido[4,5-b][1,4]diazepin-4-amines which are useful for inhibiting protein kinases.

BACKGROUND OF THE INVENTION

Protein tyrosine kinases (PTKs) are enzymes which catalyse the phosphorylation of specific tyrosine residues in cellular proteins. This post-translational modification of proteins acts as a molecular switch regulating cell proliferation, differentiation, metabolism, migration, and survival. Aberrant or excessive PTK activity has been observed in many disease states including benign and malignant proliferative disorders as well as diseases resulting from inappropriate activation of the immune system (e.g., autoimmune disorders), allograft rejection, and graft versus host disease. In addition, endothelial-cell specific PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment, the present invention provides compounds of Formula (I)

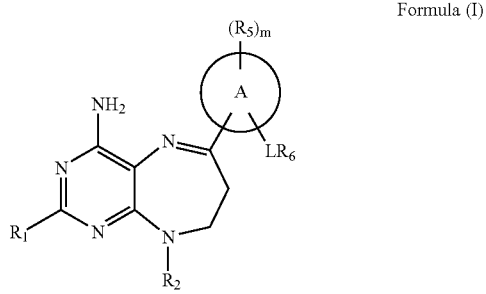

Formula (I)

or a therapeutically acceptable salt thereof, wherein $R_1$, is selected from the group consisting of hydrogen and $NH_2$;

$R_2$ is selected from the group consisting of hydrogen, alkoxycarbonyl, alkyl, alkylcarbonyl, arylalkoxycarbonyl, and heterocyclealkyl;

A is selected from the group consisting of phenyl and pyridinyl;

L is selected from the group consisting of —$(CH_2)_n N(R_3)C(O)$—, —$N(R_3)C(O)(CH_2)_n$—, and —$(CH_2)_n N(R_3)C(O)N(R_4)$—;

n is 0, 1, 2, 3, 4, 5 or 6;

$R_3$ and $R_4$ are independently selected from the group consisting of hydrogen and alkyl $R_5$ is independently selected from the group consisting of alkenyl, alkoxy, alkoxycarbonyl, alkyl, alkynyl, haloalkoxy, haloalkyl, halogen, hydroxy, hydroxyalkyl, and $NR_A R_B$;

m is 0, 1, 2, 3, or 4;

$R_6$ is selected from the group consisting of aryl, arylalkenyl, arylalkyl, cycloalkyl, cycloalkylalkenyl, cycloalkylalkyl, heteroaryl, heteroarylalkenyl, heteroarylalkyl, heterocycle, heterocyclealkenyl, and heterocyclealkyl; and $R_A$ and $R_B$ are independently selected from the group consisting of hydrogen and alkyl.

In another embodiment, the present invention provides a pharmaceutical composition comprising a compound of Formula (I), or a therapeutically acceptable salt thereof, in combination with a therapeutically acceptable carrier.

In another embodiment, the present invention provides a method for inhibiting protein tyrosine kinases in a patient in recognized need of such treatment comprising administering to the patient a therapeutically acceptable amount of a compound of Formula (I), or a therapeutically acceptable salt thereof.

In another embodiment, the present invention provides a method for inhibiting receptor protein tyrosine kinases in a patient in recognized need of such treatment comprising administering to the patient a therapeutically acceptable amount of a compound of Formula (I), or a therapeutically acceptable salt thereof.

In another embodiment, the present invention provides a method for inhibiting receptor protein tyrosine kinases modulated by vascular endothelial growth factor (VEGF) in a patient in recognized need of such treatment comprising administering to the patient a therapeutically acceptable amount of a compound of Formula (I), or a therapeutically acceptable salt thereof.

In another embodiment, the present invention provides a method for inhibiting receptor protein tyrosine kinases modulated by platelet derived growth factor (PDGF) in a patient in recognized need of such treatment comprising administering to the patient a therapeutically acceptable amount of a compound of Formula (I), or a therapeutically acceptable salt thereof.

In another embodiment, the present invention provides a method for inhibiting receptor protein tyrosine kinases modulated by vascular endothelial growth factor (VEGF) and platelet derived growth factor (PDGF) in a patient in recognized need of such treatment comprising administering to the patient a therapeutically acceptable amount of a compound of Formula (I), or a therapeutically acceptable salt thereof.

DETAILED DESCRIPTION OF THE INVENTION

In another embodiment, the present invention provides a compound of Formula (I) wherein A is phenyl; L is —$(CH_2)_n N(R_3)C(O)N(R_4)$—; n is 0; $R_6$ is aryl; and m, $R_1$, $R_2$, $R_3$, $R_4$, and $R_5$ are as defined in Formula (I).

In another embodiment, the present invention provides a compound of Formula (I) wherein A is phenyl; $R_1$, $R_2$, $R_3$, and $R_4$ are each hydrogen; m is 0 or 1; $R_5$ is alkyl when m is 1; L is —$(CH_2)_nN(R_3)C(O)N(R_4)$—; n is 0; $R_6$ is aryl wherein the aryl is phenyl optionally substituted with 1 or 2 substituents selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl; and $Z_1$ and $Z_2$ are independently selected from the group consisting of hydrogen and carbon.

In another embodiment, the present invention provides a compound of Formula (I) wherein A is phenyl; $R_1$, $R_2$, $R_3$, and $R_4$ are each hydrogen; m is 0 or 1; $R_5$ is alkyl when m is 1; L is —$(CH_2)_nN(R_3)C(O)N(R_4)$—; n is 0; $R_6$ is aryl wherein the aryl is phenyl optionally substituted with 1 or 2 substituents selected from the group consisting of alkyl, haloalkyl, and halogen.

In another embodiment, the present invention provides a compound of Formula (I) wherein A is phenyl; $R_1$, $R_3$, and $R_4$ are each hydrogen; m is 0 or 1; $R_2$ is heterocyclealkyl; $R_5$ is alkyl when m is 1; L is —$(CH_2)_nN(R_3)C(O)N(R_4)$—; n is 0; $R_6$ is aryl wherein the aryl is phenyl optionally substituted with 1 or 2 substituents selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl; and $Z_1$ and $Z_2$ are independently selected from the group consisting of hydrogen and carbon.

In another embodiment, the present invention provides a compound of Formula (I) wherein A is phenyl; $R_1$, $R_3$, and $R_4$ are each hydrogen; m is 0 or 1; $R_2$ is heterocyclealkyl wherein the heterocycle of heterocyclealkyl is selected from the group consisting of azepanyl, diazepanyl, morpholinyl, piperazinyl, piperidinyl, and pyrrolidinyl; $R_5$ is alkyl when m is 1; L is —$(CH_2)_nN(R_3)C(O)N(R_4)$—; n is 0; $R_6$ is aryl wherein the aryl is phenyl optionally substituted with 1 or 2 substituents selected from the group consisting of alkyl, haloalkyl, and halogen.

In another embodiment, the present invention provides a compound of Formula (I) wherein A is phenyl; L is —$(CH_2)_nN(R_3)C(O)$—; n is 0; $R_6$ is arylalkenyl; and m, $R_1$, $R_2$, $R_3$, and $R_5$ are as defined in Formula (I).

In another embodiment, the present invention provides a compound of Formula (I) wherein A is phenyl; $R_1$, $R_2$, and $R_3$ are each hydrogen; m is 0 or 1; $R_5$ is alkyl when m is 1; L is —$(CH_2)_nN(R_3)C(O)$; n is 0; $R_6$ is arylalkenyl wherein the aryl of arylalkenyl is phenyl optionally substituted with 1 or 2 substituents selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl; and $Z_1$ and $Z_2$ are independently selected from the group consisting of hydrogen and carbon.

In another embodiment, the present invention provides a compound of Formula (I) wherein A is phenyl; $R_1$, $R_2$, and $R_3$ are each hydrogen; m is 0 or 1; $R_5$ is alkyl when m is 1; L is —$(CH_2)_nN(R_3)C(O)$; n is 0; $R_6$ is arylalkenyl wherein the aryl of arylalkenyl is phenyl optionally substituted with 1 or 2 substituents selected from the group consisting of alkyl, haloalkyl, and halogen.

In another embodiment, the present invention provides a compound of Formula (I) wherein A is pyridinyl; L is —$(CH_2)_nN(R_3)C(O)N(R_4)$—; n is 0; $R_6$ is aryl; and m, $R_1$, $R_2$, $R_3$, $R_4$, and $R_5$ are as defined in Formula (I).

In another embodiment, the present invention provides a compound of Formula (I) wherein A is pyridinyl; $R_1$, $R_2$, $R_3$, and $R_4$ are each hydrogen; m is 0 or 1; $R_5$ is alkyl when m is 1; L is —$(CH_2)_nN(R_3)C(O)N(R_4)$—; n is 0; $R_6$ is aryl wherein the aryl is phenyl optionally substituted with 1 or 2 substituents selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl; and $Z_1$ and $Z_2$ are independently selected from the group consisting of hydrogen and carbon.

In another embodiment, the present invention provides a compound of Formula (I) wherein A is pyridinyl; $R_1$, $R_2$, $R_3$, and $R_4$ are each hydrogen; m is 0 or 1; $R_5$ is alkyl when m is 1; L is —$(CH_2)_nN(R_3)C(O)N(R_4)$—; n is 0; and $R_6$ is aryl wherein the aryl is phenyl optionally substituted with 1 or 2 substituents selected from the group consisting of alkyl, haloalkyl, and halogen.

In another embodiment, the present invention provides a use of a compound of Formula (I), or a therapeutically acceptable salt thereof, to prepare a medicament for inhibiting protein tyrosine kinases in a mammal in recognized need of such treatment.

In another embodiment, the present invention provides a use of a compound of Formula (I), or a therapeutically acceptable salt thereof, to prepare a medicament for inhibiting receptor protein tyrosine kinases in a mammal in recognized need of such treatment.

In another embodiment, the present invention provides a use of a compound of Formula (I), or a therapeutically acceptable salt thereof, to prepare a medicament for inhibiting receptor protein tyrosine kinases modulated by vascular endothelial growth factor (VEGF) in a mammal in recognized need of such treatment.

In another embodiment, the present invention provides a use of a compound of Formula (I), or a therapeutically acceptable salt thereof, to prepare a medicament for inhibiting receptor protein tyrosine kinases modulated by platelet derived growth factor (PDGF) in a mammal in recognized need of such treatment.

In another embodiment, the present invention provides a use of a compound of Formula (I), or a therapeutically acceptable salt thereof, to prepare a medicament for inhibiting receptor protein tyrosine kinases modulated by vascular endothelial growth factor (VEGF) and platelet derived growth factor (PDGF) in a mammal in recognized need of such treatment.

Definitions

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl.

The term "arylalkenyl" as used herein, means an aryl group, as defined herein, appended to the parent molecular moiety through an alkenyl group, as defined herein. Representative examples of arylalkenyl include, but are not limited to, 2-phenylvinyl, 3-phenylprop-2-enyl, and 4-phenylbut-2-enyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(O)- group.

The term "carboxy" as used herein, means a —$CO_2$H group.

The term "cyano" as used herein, means a —CN group.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, oxo, $NZ_1Z_2$, and $(NZ_1Z_2)$carbonyl.

The term "cycloalkylalkenyl" as used herein, means a cycloalkyl group, as defined herein, appended to the parent molecular moiety through an alkenyl group, as defined herein.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring fused to a cycloalkyl group or the 5 or 6 membered heteroaryl ring fused to a cycloalkenyl group or the 5 or 6 membered heteroaryl ring fused to another 5 or 6 membered heteroaryl ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, 5,6-dihydroisoquinolinyl, 7,8-dihydroisoquinolinyl, 5,6-dihydroquinolinyl, 7,8-dihydroquinolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, 5,6,7,8-tetrahydroisoquinolinyl, 5,6,7,8-tetrahydroquinolinyl, tetrazolyl, thiadiazolyl, thiazolyl, thienopyridinyl, thienyl, triazolyl, and triazinyl.

The heteroaryl groups of the present invention are optionally substituted with 1, 2, 3, or 4 substituents independently selected from alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, $NZ_1Z_2$, and $(NZ_1Z_2)$carbonyl.

The term "heteroarylalkenyl" as used herein, means a heteroaryl, as defined herein, appended to the parent molecular moiety through an alkenyl group, as defined herein.

The term "heteroarylalkyl" as used herein, means a heteroaryl, as defined herein, appended to the parent molecular moiety through an alkyl group, as defined herein.

The term "heterocycle" or "heterocyclic" as used herein, means a monocyclic heterocyclic ring or a bicyclic heterocyclic ring. The monocyclic heterocyclic ring consists of a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a phenyl group or the monocyclic heterocyclic ring fused to a cycloalkyl group or the monocyclic heterocyclic ring fused to a cycloalkenyl group or the monocyclic heterocyclic ring fused to another monocyclic heterocyclic ring. Representative examples of the bicyclic heterocyclic ring include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocycles of this invention are optionally substituted with 1, 2, or 3 substituents independently selected from alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, oxo, $NZ_1Z_2$, and $(NZ_1Z_2)$carbonyl.

The term "heterocyclealkenyl" as used herein, means a heterocycle, as defined herein, appended to the parent molecular moiety through an alkenyl group, as defined herein.

The term "heterocyclealkyl" as used herein, means a heterocycle, as defined herein, appended to the parent molecular moiety through an alkyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "$NR_AR_B$" as used herein, means two groups, $R_A$ and $R_B$, which are appended to the parent molecular moiety through a nitrogen atom. $R_A$ and $R_B$ are each independently selected from the group consisting of hydrogen and alkyl. Representative examples of $NR_AR_B$ include, but are not limited to, amino, methylamino, dimethylamino, methylethylamino, and diethylamino.

The term "$NZ_1Z_2$" as used herein, means two groups, $Z_1$ and $Z_2$, which are appended to the parent molecular moiety through a nitrogen atom. $Z_1$ and $Z_2$ are each independently selected from the group consisting of hydrogen, alkyl, alkylcarbonyl, and formyl. Representative examples of $NZ_1Z_2$ include, but are not limited to, amino, methylamino, acetylamino, acetylmethylamino, dimethylamino, and methylethylamino.

The term "$(NZ_1Z_2)$carbonyl" as used herein, means a $NZ_1Z_2$ group, as defined herein, appended to the parent molecular moiety through a carbonyl group, as defined herein. Representative examples of $(NZ_1Z_2)$carbonyl include, but are not limited to, aminocarbonyl, (methylamino)carbonyl, (dimethylamino)carbonyl, and (ethylmethylamino)carbonyl.

The term "oxo" as used herein, means a=O moiety.

Compounds of the present invention were named by ACD/ChemSketch version 5.03 (developed by Advanced Chemistry Development, Inc., Toronto, ON, Canada) or were given names which appeared to be consistent with ACD nomenclature.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a compound of the present invention with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, nitrogen atoms in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of Formula (I) for example, by hydrolysis in blood.

When it is possible that, for use in therapy, therapeutically effective amounts of a compound of Formula (I), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of Formula (I), or therapeutically acceptable salts thereof, and one or more pharmaceutically acceptable carriers, diluents, or excipients. The carrier(s), diluent(s), or excipient(s) must be acceptable in the sense of being compatible with the other ingredients of the formulation and not deleterious to the recepient thereof. In accordance with another aspect of the invention there is also provided a process for the preparation of a pharmaceutical formulation including admixing a compound of Formula (I), or a therapeutically acceptable salt thereof, with one or more pharmaceutically acceptable carriers, diluents, or excipients.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of Formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier (s) or excipient(s). In addition, compounds of the present invention can be administered using conventional drug delivery technology, for example, intra-arterial stents.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by cumminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound of Formula (I), suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an altenative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and therapeutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of Formula (I), and therapeutically acceptable salts thereof, may also be delivered by the use of monoclonal antibodies as individual carriers to which the compound molecules are coupled. The compounds of Formula (I) may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds of Formula (I) may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the above-mentioned conditions. In particular, in anti-cancer therapy, combination with other chemotherapeutic, hormonal, or antibody agents is envisaged as well as combination with surgical therapy and radiotherapy. Combination therapies according to the present invention thus comprise the administration of at least one compound of Formula (I), or a therapeutically acceptable salt thereof, and the use of at least one other cancer treatment method. Preferably, combination therapies according to the present invention comprise the administration of at least one other pharmaceutically active agent, preferably an anti-neoplastic agent. The compound(s) of Formula (I) and the other pharmaceutically active agent(s) may be administered together or separately and when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

The compounds of Formula (I), or therapeutically acceptable salts thereof, and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of Formula (I), or therapeutically acceptable salts thereof, with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts of Formula (I) include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, and thioguanine; and camptothecins such as 9-amino camptothecin, irinotecan, topotecan, CPT-11, and the various optical forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor, erb-B2, erb-B4, epidermal growth factor receptor (EGFR), platelet derived growth factor receptor (PDGFR), vascular endothelial growth factor receptor (VEGFR and TIE-2 (other than those VEGFR and TIE-2 inhibitors described in the present invention)); and other tyrosine kinase inhibitors such as inhibitors of CDK2 and CDK4 inhibitors.

In Vitro Determination of Biological Activity

The potency of compounds of the present invention at inhibiting phosphorylation of exogenous substrates was determined by the procedures described herein.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at $2\times10^6$/ml, and were infected at 0.5 plaque forming units per cell (MOI). Cells were harvested at 48 hours post infection.

Purification of KDR

SF-9 cells expressing $(His)_6$ KDR(aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-His6 sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at $2\times10^6$/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (500 units/50 μL) and the EGF ligand was acquired from Oncogene Research Products/Calbiochem.

Protein Kinase Source

Lck, Fyn, Src, Blk, Csk, and Lyn, and truncated forms thereof may be commercially obtained (e.g., from Upstate Biotechnology Inc. and Santa Cruz Biotechnology Inc.) or purified from known natural or recombinant sources using conventional methods.

Homogenous Time-resolved Fluorescence (HTRF) In vitro Kinase Assay (Mathis, G., HTRF(R) Technology. J Biomol Screen, 1999. 4(6): p. 309-314; Alfred J. Kolb, Paul V. Kaplita, David J. Hayes, Young-Whan Park, Christine Pernell, John S. Major and Gérard Mathis, Drug Discovery Today, 1998, 3, 333-342.):

For example, purified enzyme was mixed with 4 μM N-biotinylated substrate (e.g., poly(Glu$_4$Tyr)) and various concentrations of a compound of the present invention in reaction buffer (50 mM HEPES, pH 7.1, 10 mM MgCl$_2$, 2 mM MnCl$_2$, 0.1% BSA and 1 mM DTT, 40 μL final volume). The kinase reaction was initiated by addition of ATP (1 mM final conc.) in a black 96-well plate (Packard). After 30-60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphosphotyrosine mAb PT66-K Europium kryptate) was added to the reaction mixture. The quenched reaction was allowed to stand at room temperature for 3 hour and then read in a time-resolved fluorescence detector (Discovery, Packard) at 620 nm and 665 nm simultaneously. A 337 nm nitrogen laser was used for excitation. The ratio between the signal of 620 nm and 665 nm was used to determine IC$_{50s}$ which are shown in Table 1 and Table 2 for compounds of the present invention.

TABLE 1

| HTRF KDR (nM) | | | |
|---|---|---|---|
| 5 | 137 | 126 | 950 |
| 65 | 3 | 49 | 6 |
| 23 | 888 | 65 | 6 |
| 19 | 12 | 3 | 110 |

TABLE 2

| HTRF cKIT (nM) | | | |
|---|---|---|---|
| 3021 | 908 | 147 | 6 |
| 36 | 12 | 31 | 11 |
| 6 | 36 | 50 | 18 |
| 22 | 6 | 35 | 28 |

More specific details for the various enzymes are included below in Table 3.

TABLE 3

| | | | HTRF ASSAYS | | | | | | |
|---|---|---|---|---|---|---|---|---|---|
| Enzyme | Construct | MW (kD) | Enz. Reaction Conc. (ng/well) | Assay Buffer | Substrate | Peptide Substrate Conc. (μM) | ATP Conc. (mM) | DMSO Conc. (%) | Reaction Time (min) |
| Lck (Truncated) | 62–509 | 52 | 2.1 | MOPSO | bio-LCK peptide | 4 | 1 | 5 | 60 |
| Src (UBI) | NA | 60 | 0.15 U/well | MOPSO | bio-LCK peptide | 4 | 1 | 5 | 60 |
| Lyn | His6-Tag | 52 | 0.5 | MOPSO | bio-LCK peptide | 4 | 1 | 5 | 60 |
| Fyn (Catalytic Domain) | His6-Tag (257–534) | 34 | 0.15 | MOPSO | bio-LCK peptide | 4 | 1 | 5 | 60 |
| Csk | His6-Tag | 50 | 0.33 | MOPSO | bio-PGT | 4 | 1 | 5 | 10 |
| Lck (Catalytic Domain) | His6-Tag | 35 | 1 | MOPSO | bio-LCK peptide | 4 | 1 | 5 | 60 |
| Blk (Catalytic Domain) | His6-Tag | 60 | 0.15 | MOPSO | bio-LCK peptide | 4 | 1 | 5 | 60 |
| KDR | His6-KDR 789–1354 | 63 | 7 | HEPES | bio-FGFR peptide | 4 | 1 | 5 | 60 |
| Tie2 | His6-Tag | 40 | 12.6 | HEPES | bio-PGT | 10 ng/well | 1 | 5 | 10 |
| cKIT | GST-Fusion | 70 | 4* | HEPES | bio-FGFR peptide | 0.5* | 1 | 5 | 60 |
| Flt1 | His6-Tag | 65 | | HEPES | bio-FGFR peptide | 4 | 1 | 5 | 60 |
| CSF-1r | M-His(6)-CSF-1R Q547–C972 | 50 | 10 | HEPES | bio-Lck peptide | 4 | 1 | 5 | 60 |

Substrates

Bio-FGFR peptide means biotin-(6-aminohexanoic acid)-FGFR peptide wherein the FGFR peptide is as described in Z. Songyang et. al., Nature, 373:536-539 (1995) except that alanine amide was added to the carboxy end.

Bio-LCK peptide means biotin-(6-aminohexanoic acid)-Lck peptide wherein the Lck peptide is as described in Z. Songyang et. al., Nature, 373:536-539 (1995) except that glycine-alanine was added to the amino end, valine was substituted for alanine at the +2 position, and alanine was truncated.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

KDR Cellular Assay

Inhibition of KDR phosphorylation in cells by compounds of the present invention was measured by ELISA following the protocol outlined below.

Day 1 Protocol

KDR transfected 3T3 (embryonic mouse) cells were added to 96-well tissue culture plates at 20,000 cells/well. Plates were covered and placed in a 37° C. humidified incubator with 5% $CO_2$ overnight, to allow cells to adhere.

Coating solution consisted of 200 µg of anti-KDR antibody in 76 µl PBS (R&D Systems) diluted into 30 mls bicarbonate buffer, added to all wells at 150 µl/well, and placed at 4° C. overnight.

Day 2 Protocol

Blocking solution, 5% milk in PBS, was placed on a stir plate for 30 min. Assay plates were washed twice with PBST, and 200 µl/well blocking solution was added to all wells. Assay plates were covered with plate sealers and placed in a 37° C. microplate chamber until just before cell lysate transfer.

Conditioned media was removed from the plates and the plates were blotted dry. DMEM was added (100 µl/well) and the plates were incubated for 2 hours to serum starve.

Compound stocks consisted of compounds of the present invention at a concentration of 5 mM in DMSO. Compound stocks in dilution medium (DM, 1% DMSO in DMEM) were diluted by half-log increments for concentration response analysis. DMEM was removed from the tissue culture plates and the plates were blotted dry. Reference inhibitor in DM, compound dilutions in DM, or DM (for high control, negative control, and reference wells) were added to the tissue culture plates, 25 µl/well. Each pair of tissue culture plates was prepared with the same compounds, solutions, and layout; and combined later. Tissue culture plates were covered and placed in the 37° C. microplate chamber for 20 minutes.

VEGF solution consisted of 110 µl VEGF stock and 10.89 ml DM (100 ng/ml VEGF). VEGF solution or DM (for reference wells) was added to the tissue culture plates, 25 µl/well. Tissue culture plates were covered and placed in the 37° C. microplate chamber for 10 minutes.

RIP A buffer, consisting of 2401 µl $NaVO_3$ stock, 240 µl PIC stock, 24 µl NaF stock, and 23.496 ml RIP A base, was added to the tissue culture plates, 50 µl/well. Tissue culture plates were covered and placed on a Labline plate shaker for 10 minutes.

Assay plates were washed twice with PBST. Cell lysates from matching wells of each pair of tissue culture plates were combined to ≈200 µl/well, and were pipetted up and down to mix. Cell lysates were transferred to the assay plates using the same layouts, 170 µl/well. Assay plates were covered with plate sealers and placed on a Labline plate shaker for 2 hr (speed about 5). Assay plates were washed 5 times with PBST.

Biotin antibody solution, consisting of 16 µl biotin antibody stock and 32 ml PBST) was added to the assay plates, 150 µl/well. Assay plates were covered with plate sealers and placed on a Labline plate shaker for about 60 minutes. Assay plates were washed 5 times with PBST. Streptavidin-HRP solution, consisting of 16 µl streptavidin-HRP stock and 32 ml PBST, was added to the assay plates, 150 µl/well. Assay plates were covered with plate sealers and placed on a Labline plate shaker for about 60 minutes. Assay plates were washed 5 times with PBST. Enhanced K-blue substrate (TMB) (Neogen) was added to the assay plates, 100 µl/well. As assay plates developed, the plates were each monitored on a Molecular Devices Spectramax set to 650 nm, until the signal in the high control wells was around 0.6 OD and the signal in the negative control wells was around 0.1-0.15 OD.

Stop solution was added to the assay plates, 100 µl/well.

The plates were read on a Molecular Devices Spectramax set to 450 nm. Data was calculated by Assay Explorer, using same-plate high control wells as 0% and reference inhibitor wells as 100% inhibition of KDR phosphorylation. The $IC_{50}$ values for compounds of the present invention were calculated by non-linear regression analysis of the concentration response data and are shown in Table 4.

TABLE 4

| KDR Cellular Assay (nM) | | | |
|---|---|---|---|
| 793 | 13 | 311 | 52 |
| 713 | 311 | | |

Reagents & Materials

All reagents are reagent grade or better and are available commercially unless otherwise indicated.

PBS consisted of 1× phosphate-buffered saline (pH 7.4) without calcium chloride and without magnesium chloride (Invitrogen/Gibco).

Anti-KDR antibody consisted of anti-human VEGF $R_2$ (KDR) antibody, (R&D Systems) 5 mg per vial at 2.630 mg/ml, divided into 38 µl aliquots and stored at −30° C.

Bicarbonate buffer consisted of 1 packet BupH carbonate-bicarbonate buffer pack (Pierce) in 500 ml water, stored at room temperature.

96-well assay plate means EIA/RIA Easywash plate, high binding, (Costar).

PBST consited of 1 ml tween 20 in 1 L PBS, stored at room temperature.

DMEM consisted of Dulbecco's modified Eagle medium, high glucose, with L-glutamine, with pyroxidine hydrochloride, and without sodium pyruvate, (Invitrogen/Gibco).

VEGF stock consisted of 1 ml PBS/BSA (PBS and 0.1% BSA, stored at room temperature) added to 1 vial VEGF (recombinant human VEGF, (R&D Systems), 10 µg per vial), divided into 55 µl aliquots, stored at −80° C.

$NaVO_3$ stock consisted of 12.19 mg/ml sodium metavanadate (Sigma) in water (100 mM) heated at 37° C. to solubilize then divided into 120 µl aliquots, stored at −20° C.

PIC stock consisted of protease inhibitor cocktail (Sigma) divided into 120 µl aliquots stored at −20° C.

NaF stock consists of 41.99 mg/ml sodium fluoride in water (1M), divided into 12 µl aliquots, stored at −20° C.

RIP A base consists of 3.94 g Trizma hydrochloride (Sigma), 5.0 ml Igepal (Sigma), 1.25 g deoxycholic acid sodium salt, 4.383 g NaCl, 226.1 mg EDTA (Sigma) combined in 500 ml water with pH adjusted to 7.4, stored at 4° C.

Biotin antibody stock consisted of anti-phosphotyrosine biotin-conjugate mouse monoclonal IgG2bκ, clone 4G10, (Upstate Biotechnology).

Streptavidin-HRP stock consisted of streptavidin horseradish peroxidase conjugate (Upstate Biotechnology).

Stop solution consisted of 14.5 ml phosphoric acid (Sigma) and 235.5 ml water, stored at room temperature.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system serves as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8-12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

The compounds of the present invention may be used in the treatment of protein tyrosine kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g,. kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (J. Thorac. Cardiovasc. Surg. 2001, 122 (1), 65-73).

This invention is intended to encompass compounds having Formula (I) when prepared by synthetic processes or by metabolic processes. Preparation of the compounds of the invention by metabolic processes include those occurring in the human or animal body (in vivo) or processes occurring in vitro.

Synthetic Methods

Abbreviations which have been used in the descriptions of the scheme and the examples that follow are: nBu for n-butyl; dppf for diphenylphosphinoferrocene; DMF for N,N-dimethylformamide; DME for 1,2-dimethoxyethane; HPLC for high pressure liquid chromatography; NMP for N-metbylpyrrolidinone; DMSO for dimethylsulfoxide; min for minutes; and THF for tetrahydrofuran.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

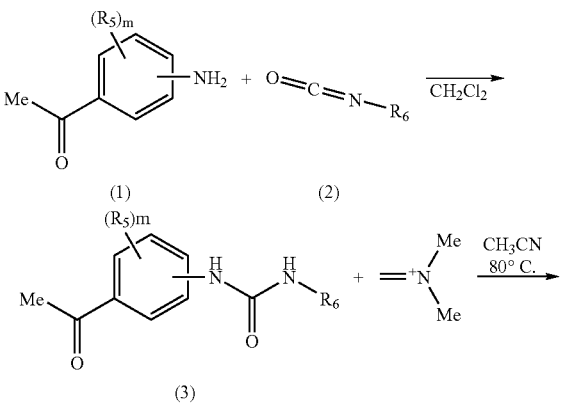

Scheme 1

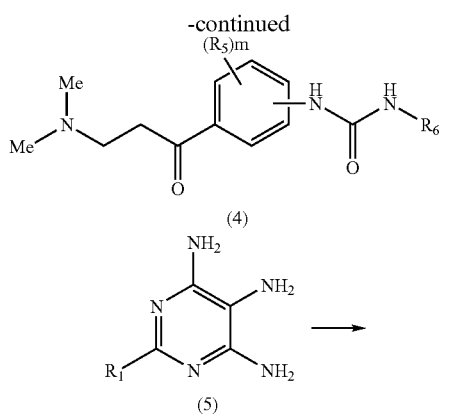
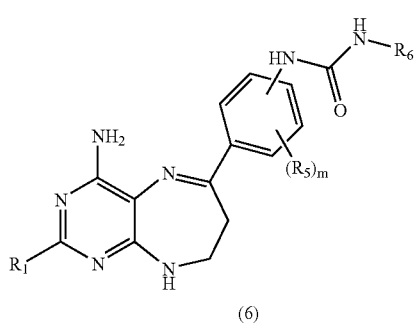
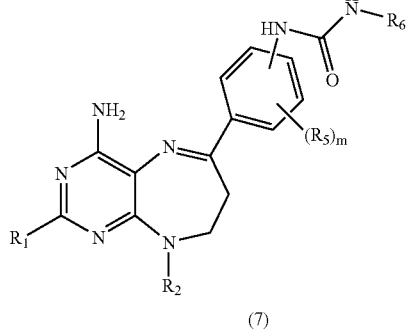

Compounds of formula (6), wherein $R_1$, $R_5$, m, and $R_6$ are as defined in Formula (I), can be prepared as described in Scheme 1. Aminobenzenes (or aminopyridines) of formula (1) can be treated with isocyanates of formula (2) in an appropriate solvent such as methylene chloride to provide ureas of formula (3). Ureas of formula (3) can be treated with N,N-dimethylmethyleneiminium iodide or chloride to provide ureas of formula (4). Ureas of formula (4) can be treated with pyrimidines of formula (5) to provide 7,8-dihydro-1H-pyrimido[4,5-b][1,4]diazepines of formula (6). 7,8-Dihydro-1H-pyrimido[4,5-b][1,4]diazepines of formula (6) can be treated with anhydrides, acid chlorides, or alkyl halides to provide 7,8-dihydro-1H-pyrimido[4,5-b][1,4]diazepines of formula (7) wherein $R_2$ is as defined in Formula (I).

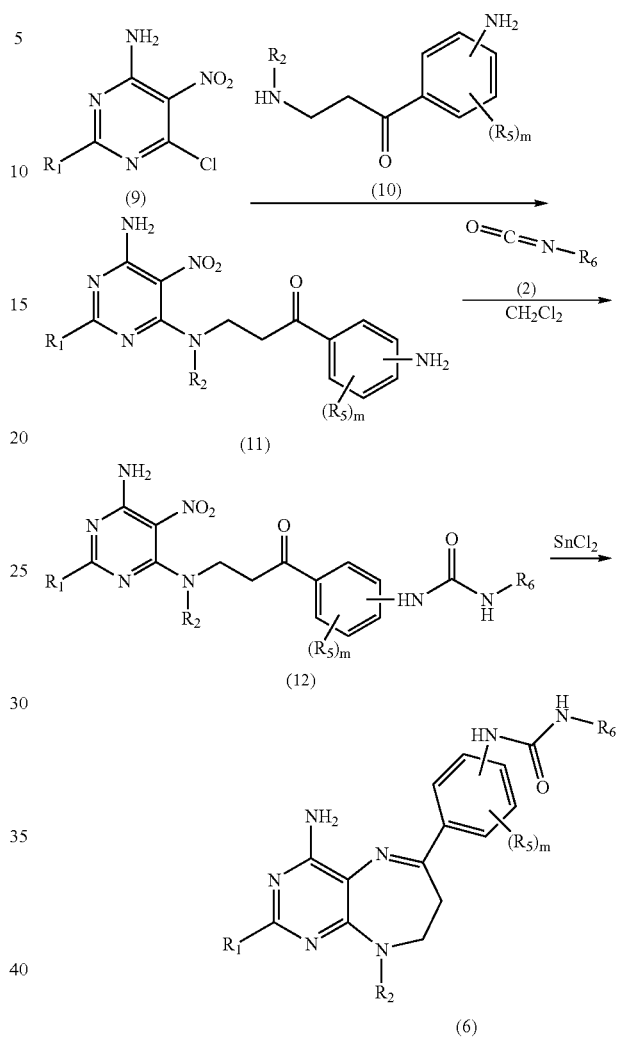

Compounds of formula (6), wherein $R_1$, $R_5$, m, and $R_6$ are as defined in Formula (I), can be prepared as described in Scheme 2. Nitro analogs of formula (9) can be treated with compounds of formula (10) in a suitable solvent such as THF to provide compounds of formula (11). Compounds of formula (11) can be treated with isocyanates of formula (2) to provide compounds of formula (12). Compounds of formula (12) can be treated with a reducing agent such as stannous chloride to provide compounds of formula (6).

EXAMPLE 1

N-[4-(4-amino-8,9-dihydro-7H-pyrimido[4,5][1,4]diazepin-6-yl)phenyl]-N'-phenylurea

EXAMPLE 1A

N-(4-acetylphenyl)-N'-phenylurea

A mixture of 4-aminoacetophenone (1.0 g, 7.40 mmol) and phenyl isocyanate (0.80 ml, 7.40 mmol) in $CH_2Cl_2$ (5.0 ml) were stirred at room temperature for 17 hours. The mixture was filtered and the filter cake washed with $CH_2Cl_2$ and dried to afford 1.0 g (53%) of Example 1A as a white solid that was used in the next step without further purification. $^1$H NMR (300 MHz, DMSO-d$_6$): δ 3.33 (s, 3H), 7.00 (t, J=9.0 Hz, 1H), 7.30 (t, J=9.0 Hz, 2H), 7.46 (d, J=6.0 Hz, 2H), 7.58 (d, J=9.0 Hz, 2H), 7.90 (d, J=9.0 Hz, 2H), 8.79 (br s, 1H), 9.08 (br s, 1H); MS (ESI) 254 (M+H).

EXAMPLE 1B

N-{4-[3-(dimethylamino)propanoyl]phenyl}-N'-phenylurea hydrochloride

A mixture of Example 1A (0.500 g, 1.96 mmol) and N,N-dimethylmethyleneiminium chloride (0.184 g, 1.96 mmol) in CH$_3$CN (10 mL) were heated at 80° C. for 17 hours, cooled to room temperature and filtered. The filter cake was washed with CH$_3$CN and dried to give Example 1B as a white solid (50%) which was used in the next step without purification. $^1$H NMR (300 MHz, DMSO-d$_6$): δ 2.81 (s, 6H), 3.40 (m, 2H), 3.53 (m, 2H), 6.99 (t, J=9.0 Hz, 1H), 7.29 (t, J=6.0 Hz, 2H), 7.47 (d, J=9.0 Hz, 2H), 7.63 (d, J=9.0 Hz, 2H), 7.96 (d, J=9.0 Hz, 2H), 9.50 (br s, 1H), 9.90 (br s, 1H).

EXAMPLE 1C

N-[4-(4-amino-8,9-dihydro-7H-pyrimido[4,5-b][1,4]diazepin-6-yl)phenyl]-N'-phenylurea A mixture of 4,5,6-triaminopyrimidine (0.1 g, 0.80 mmol) and Example 1B (0.248 g, 0.80 mmol) in EtOH (5 mL) was heated at reflux for 15 hours, cooled to room temperature, filtered and the filtrate was concentrate. The residue was purified by preparative HPLC on a Waters Symmetry C8 column (25 mm×100 mm, 7 μm particle size) using a gradient of 10% to 100% acetonitrile/10 mmol ammonium acetate over 8 minutes (10 minute run time) at a flow rate of 40 mL/minute to give the title compound. $^1$H NMR (500 MHz, DMSO-d$_6$): δ 3.08 (m, 2H), 3.42 (m, 2H), 6.44 (br s, 2H), 6.97 (t, J=5.0 Hz, 1H), 7.11 (br s, 1H), 7.28 (t, J=5.0 Hz, 2H), 7.47 (d, J=5.0 Hz, 2H), 7.52 (d, J=10.0 Hz, 2H), 7.68 (s, 1H), 7.92 (d, J=10.0 Hz, 2H), 8.95 (br s, 1H), 9.13 (br s, 1H); MS (ESI) 374 (M+H).

EXAMPLE 2

N-[3-(4-amino-8,9-dihydro-7H-pyrimido[4,5-b][1,4]diazepin-6-yl)phenyl]-N'-phenylurea The title compound was prepared using the procedures described in Examples 1A-C, substituting 3-aminoacetophenone for 4-aminoacetophenone in Example 1A. $^1$H NMR (500 MHz, DMSO-d$_6$): δ 3.10 (m, 2H), 3.42 (m, 2H), 6.49 (brs, 2H), 6.95 (m, 1H), 7.20-7.33 (m, 5H), 7.44-7.52 (m, 4H), 8.06 (s, 1H), 9.35 (brs, 1H), 9.40 (brs, 1H); MS (ESI) 374 (M+H).

EXAMPLE 3

N-[3-(4-amino-8,9-dihydro-7H-pyrimido[4,5-b][1,4]diazepin-6-yl)phenyl]-N'-[3-(trifluoromethyl)phenyl]urea The title compound was prepared using the procedures described in Examples 1A-C, substituting 3-aminoacetophenone for 4-aminoacetophenone and substituting 1-isocyanato-3-trifluoromethylbenzene for phenyl isocyanate in Example 1A. $^1$H NMR (400 MHz, DMSO-d$_6$): δ 3.11 (m, 2H), 3.42 (m, 2H), 6.50 (br s, 2H), 7.22 (br s, 1H), 7.28-7.35 (m, 2H), 7.50 (m, 2H), 7.63 (m, 2H), 7.70 (s, 1H), 8.03 (m, 2H), 9.43 (br s, 1H), 9.67 (br s, 1H); MS (ESI) 442 (M+H).

EXAMPLE 4

N-[3-(4-amino-8,9-dihydro-7H-pyrimido[4,5-b][1,4]diazepin-6-yl)phenyl]-N'-(4-fluoro-3-methylphenyl)urea The title compound was prepared using the procedures described in Examples 1A-C, substituting 3-aminoacetophenone for 4-aminoacetophenone and substituting 1-fluoro-4-isocyanato-2-methyl-benzene for phenyl isocyanate in Example 1A. $^1$H NMR (400 MHz, DMSO-d$_6$): δ 2.21 (s, 3H), 3.10 (m, 2H), 3.42 (m, 2H), 6.49 (br s, 2H), 7.03 (t, J=8.0 Hz, 1H), 7.20-7.31 (m, 3H), 7.39 (m, 1H), 7.50 (d, J=8.0 Hz, 1H), 7.58 (d, J=8.0 Hz, 1H), 7.70 (s, 1H), 8.02 (s, 1H), 9.03 (br s, 1H), 9.11 (br s, 1H); MS (ESI) 407 (M+H).

EXAMPLE 5

N-[4-(4-amino-8,9-dihydro-7H-pyrimido[4,5-b][1,4]diazepin-6-yl)phenyl]-N'-[3-(trifluoromethyl)phenyl]urea The title compound was prepared using the procedures described in Examples 1A-C, substituting 1-isocyanato-3-trifluoromethylbenzene for phenyl isocyanate in Example 1A. $^1$H NMR (300 MHz, DMSO-D$_6$) δ ppm 3.03-3.15 (m, 2H), 3.36-3.49 (m, 2H), 6.45 (s, 2H), 7.12 (t, J=3.90 Hz, 1H), 7.32 (d, J=7.80 Hz, 1H), 7.47-7.64 (m, 4H), 7.68 (s, 1H), 7.93 (d, J=8.82 Hz, 2H), 8.02 (s, 1H), 9.09 (s, 1H), 9.16 (s, 1H). MS(ESI(+)) m/e 442 (M+H)$^+$.

EXAMPLE 6

N-[4-(4-amino-8,9-dihydro-7H-pyrimido[4,5-b][1,4]diazepin-6-yl)phenyl]-N'-(2-fluoro-5-methylphenyl)urea The title compound was prepared using the procedures described in Examples 1A-C, substituting 1-fluoro-2-isocyanato-4-methylbenzene for phenyl isocyanate in Example 1A. $^1$H NMR (500 MHz, DMSO-D$_6$) δ ppm 2.50 (s, 3H), 3.01-3.16 (m, 2H), 3.38-3.51 (m, 2H), 6.45 (s, 2H), 6.80 (s, 2H), 7.01-7.22 (m, 2H), 7.50 (d, J=8.85 Hz, 2H), 7.68 (s, 1H), 7.93 (d, J=8.85 Hz, 2H), 8.51 (s, 1H), 9.26 (s, 1H). MS(ESI(+)) m/e 406 (M+H)$^+$.

EXAMPLE 7

N-[5-(4-amino-8,9-dihydro-7H-pyrimido[4,5][1,4]diazepin-6-yl)-2-methylphenyl]-N'-[3-(trifluoromethyl)phenyl]urea

EXAMPLE 7A 1-(3-amino-4-methylphenyl)ethanone

A mixture of 1-(4-methyl-3-nitrophenyl)ethanone (5.37 g, 30 mmol), iron powder (8.4 g, 150 mmol) and NH$_4$Cl (1.62 g, 30 mmol) in ethanol (100 mL) and water (10 mL) was heated at 80° C. overnight. The mixture was then heated at 110° C. for 5 hours and allowed to cool to room temperature. The resulting suspension was filtered and the filter cake was washed with ethanol. The filtrate was concentrated and the residue was dissolved in ethanol and filtered. The filtrate was concentrated to give 4 g of the title compound as a yellow solid. MS(ESI(+)) m/e 149.8 (M+H)+.

EXAMPLE 7B

N-[5-(4-amino-8,9-dihydro-7H-pyrimido[4,5][1,4] diazepin-6-yl)-2-methylphenyl]-N'-[3-(trifluoromethyl)phenyl]urea The title compound was prepared using the procedures described in Examples 1A-C, substituting Example 7A for 4-aminoacetophenone and substituting 1-isocyanato-3-trifluoromethylbenzene for phenyl isocyanate in Example 1A. $^1$H NMR (300 MHz, DMSO-D$_6$) δ ppm 2.30 (s, 3H), 3.17-3.25 (m, 2H), 3.48-3.59 (m, 2H), 7.30 (t, J=8.48 Hz, 2H), 7.47-7.69 (m, 3H), 7.72 (dd, J=7.97, 1.86 Hz, 2H), 8.04 (s, 1H), 8.08 (s, 1H), 8.16 (s, 1H), 8.35 (d, J=1.70 Hz, 1H), 8.57 (s, 1H), 9.43 (s, 1H). MS(ESI(+)) m/e 456 (M+H)+.

EXAMPLE 8

N-[5-(4-amino-8,9-dihydro-7H-pyrimido[4,5-b][1,4] diazepin-6-yl)-2-methylphenyl]-N'-(2-fluoro-5-methylphenyl)urea The title compound was prepared using the procedures described in Examples 1A-C, substituting Example 7A for 4-aminoacetophenone and substituting 1-fluoro-2-isocyanato-4-methylbenzene for phenyl isocyanate in Example 1A. $^1$H NMR (300 MHz, DMSO-D$_6$) δ ppm 2.27 (s, 3H), 2.31 (s, 3H), 3.16-3.24 (m, 2H), 3.50-3.59 (m, 2H), 6.72-6.84 (m, 1H), 7.11 (dd, J=11.53, 8.14 Hz, 1H), 7.27 (d, J=8.48 Hz, 2H), 7.70 (dd, J=7.80, 1.70 Hz, 2H), 8.01 (dd, J=8.14, 1.70 Hz, 1H), 8.10 (s, 1H), 8.43 (d, J=1.70 Hz, 1H), 8.47 (s, 1H), 8.62 (s, 1H), 8.95 (d, J=2.37 Hz, 1H). MS(ESI(+)) m/e 420 (M+H)+.

EXAMPLE 9

N-[4-(4-amino-8,9-dihydro-7H-pyrimido[4,5-b][1,4] diazepin-6-yl)phenyl]-N'-[2-fluoro-5-(trifluoromethyl)phenyl]urea

EXAMPLE 9A

N-{(4-[3-(1,3-Dioxo-1,3-dihydro-isoindol-2-yl)propionyl]phenyl}acetamide

N-[4-(3-chloro-propionyl)phenyl]acetamide (1.45 g, J. Med. Chem. 8, 1965, 877) and potassium phthalimide (1.31 g) were combined in DMF (5 mL) and heated at 125 C for 30 min, allowed to cool to room temperature diluted with ice water. The suspension was filtered and the filter cake was washed with water and hexanes. The precipitate in a mimimum amount of EtOAc was triturated with hexanes to give 2 g of the title compound. MS (ESI(+)) m/e 337.1 (M+H)+.

EXAMPLE 9B

3-Amino-1-(4-amino-phenyl)-propan-1-one dihydrochloride

Example 9A (2.0 g) in acetic acid (12 mL) and concentrated HCl (10 mL) was refluxed for 28 h, allowed to cool to room temperature, and concentrated. The residue was suspended in water, filtered and the filtrate was concentrated, washed with diethyl ether and ethanol to give 1 g (72% yield) of the title compound. MS(ESI(+)) m/e 165.1 (M+H)+.

EXAMPLE 9C 1-(4-Aminophenyl)-3-(6-aminopyrimidin-4-ylamino)propan-1-one

6-Chloro-5-nitro-pyrimidin-4-ylamine (379 mg, 2.1 mmol) in THF (2 mL) was added to an ice cold solution of Example 9B (510 mg, 2.1 mmol) in THF (20 mL) and ethanol (20 mL). The mixture was stirred at 0 C for 20 min, at room temperature for 1 hr and heated at 75 C for 2 h. The mixture was allowed to cool to room temperature, diluted with water (50 mL), concentrated, and filtered. The filter cake was washed with water and dried to give 0.55 g (83% yield) of the title compound. MS(ESI(+)) m/e 303.0 (M+H)+.

EXAMPLE 9D

1-{4-[3-(6-Amino-5-nitro-pyrimidin-4-ylamino) propionyl]phenyl}-3-(2-fluoro-5-trifluoromethylphenyl)urea An ice cold solution of Example 9C (91 mg, 0.3 mmol) in DMF (2 mL) was treated with 1-fluoro-2-isocyanato-4-trifluoromethylbenzene (0.046 mL), stirred at 5 C for 30 min then at room temperature overnight. The suspension was partitioned between water and EtOAc (2×) and the combined organic extracts were dried (Na$_2$SO$_4$) and concentrated. The residue was triturated with EtOAc-hexanes to give 86 mg (56% yield) of the title compound. MS(ESI(+)) m/e 508.0 (M+H)+.

EXAMPLE 9E

N-[4-(4-amino-8,9-dihydro-7H-pyrimido[4,5-b][1,4] diazepin-6-yl)phenyl]-N'-[2-fluoro-5-(trifluoromethyl)phenyl]urea Example 9D (76 mg, 0.15 mmol) in ethanol (3 mL) was treated with SnCl$_2$.2H$_2$O (226 mg, 1 mmol), heated at 80 C for 3 h, cooled to room temperature and filtered. The solid collected was dissolved in EtOAc, washed with sat. aq. NaHCO$_3$, brine, dried (MgSO$_4$) and concentrated. The residue was triturated from EtOAc-hexanes to give 19 mg of the title compound. $^1$H NMR (300 MHz, DMSO-D$_6$) δ ppm 3.04-3.12 (m, 2H), 3.38-3.48 (m, 2H), 6.44 (s, 2H), 7.13 (t, J=3.90 Hz, 1H), 7.33-7.58 (m, 4H), 7.68 (s, 1H), 7.94 (d, J=8.48 Hz, 2H), 8.62 (dd, J=7.12, 2.03 Hz, 1H), 8.92 (d, J=2.71 Hz, 1H), 9.37 (s, 1H). MS(ESI(+)) m/e 460 (M+H)+.

EXAMPLE 10

N-[4-(4-amino-8,9-dihydro-7H-pyrimido[4,5-b][1,4] diazepin-6-yl)phenyl]-N'-[3-(trifluoromethyl)phenyl] urea The title compound was prepared using the procedures described in Examples 9D and 9E except using 1-isocyanato-3-trifluoromethylbenzene instead of 1-fluoro-2-isocyanato-4-trifluoromethylbenzene in Example 9D. $^1$H NMR (300 MHz, DMSO-D$_6$) δ ppm 3.03-3.15 (m, 2H), 3.36-3.49 (m, 2H), 6.45 (s, 2H), 7.12 (t, J=3.90 Hz, 1H), 7.32 (d, J=7.80 Hz, 1H), 7.47-7.64 (m, 4H), 7.68 (s, 1H), 7.93 (d, J=8.82 Hz, 2H), 8.02 (s, 1H), 9.09 (s, 1H), 9.16 (s, 1H).
MS(ESI(+)) m/e 442 (M+H)+.

EXAMPLE 11

N-[4-(4-amino-8,9-dihydro-7H-pyrimido[4,5-b][1,4]diazepin-6-yl)phenyl]-N'-(2-fluoro-5-methylphenyl)urea The title compound was prepared using the procedures described in Examples 9D and 9E except using 1-fluoro-2-isocyanato-4-methylbenzene instead of 1-fluoro-2-isocyanato-4-trifluoromethylbenzene in Example 9D. $^1$H NMR (500 MHz, DMSO-D$_6$) δ ppm 2.50 (s, 3H), 3.01-3.16 (m, 2H), 3.38-3.51 (m, 2H), 6.45 (s, 2H), 6.80 (s, 2H), 7.01-7.22 (m, 2H), 7.50 (d, J=8.85 Hz, 2H), 7.68 (s, 1H), 7.93 (d, J=8.85 Hz, 2H), 8.51 (s, 1H), 9.26 (s, 1H). MS(ESI(+)) m/e 406 (M+H)+.

EXAMPLE 12

N-[4-(4-amino-8,9-dihydro-7H-pyrimido[4,5-b][1,4]diazepin-6-yl)phenyl]-N'-[4-chloro-3-(trifluoromethyl)phenyl]urea The title compound was prepared using the procedures described in Examples 9D and 9E except using 1-chloro-4-isocyanato-2-trifluoromethylbenzene instead of 1-fluoro-2-isocyanato-4-trifluoromethylbenzene in Example 9D. $^1$H NMR (300 MHz, DMSO-D$_6$) δ ppm 3.04-3.15 (m, 2H), 3.37-3.49 (m, J=4.41 Hz, 2H), 6.58 (s, 2H), 7.21-7.33 (m, 1H), 7.52 (d, J=8.82 Hz, 2H), 7.59-7.71 (m, 2H), 7.73 (s, 1H), 7.94 (d, J=8.82 Hz, 2H), 8.11 (d, J=2.03 Hz, 1H), 9.09 (s, 1H), 9.23 (s, 1H). MS(ESI(+)) m/e 476 (M+H)+.

EXAMPLE 13

N-[4-(4-amino-8,9-dihydro-7H-pyrimido[4,5-b][1,4]diazepin-6-yl)phenyl]-N'-(3-chlorophenyl)urea The title compound was prepared using the procedures described in Examples 9D and 9E except using 1-chloro-3-isocyanatobenzene instead of 1-fluoro-2-isocyanato-4-trifluoromethylbenzene in Example 9D. $^1$H NMR (300 MHz, DMSO-D$_6$) δ ppm 3.10-3.24 (m, 2H), 3.48-3.59 (m, 2H), 6.96-7.10 (m, 1H), 7.22-7.37 (m, 2H), 7.55 (d, J=8.81 Hz, 2H), 7.67-7.82 (m, 3H), 8.03 (d, J=9.15 Hz, 2H), 8.07 (s, 1H), 8.50 (s, 1H), 9.15 (s, 1H), 9.23 (s, 1H).
MS(ESI(+)) m/e 408 (M+H)+.

EXAMPLE 14

N-[4-(4-amino-8,9-dihydro-7H-pyrimido[4,5-b][1,4]diazepin-6-yl)phenyl]-N'-[4-fluoro-3-(trifluoromethyl)phenyl]urea The title compound was prepared using the procedures described in Examples 9D and 9E except using 1-fluoro-4-isocyanato-2-trifluoromethylbenzene instead of 1-fluoro-2-isocyanato-4-trifluoromethylbenzene in Example 9D. $^1$H NMR (300 MHz, DMSO-D$_6$) δ ppm 3.14-3.26 (m, 2H), 3.49-3.60 (m, 2H), 7.45 (t, J=9.83 Hz, 1H), 7.56 (d, J=9.15 Hz, 2H), 7.61-7.72 (m, 1H), 7.79 (s, 2H), 7.97-8.07 (m, 3H), 8.09 (s, 1H), 8.55 (s, 1H), 9.33 (s, 1H), 9.37 (s, 1H).
MS(ESI(+)) m/e 460 (M+H)+.

EXAMPLE 15

N-[4-(4-amino-8,9-dihydro-7H-pyrimido[4,5-b][1,4]diazepin-6-yl)phenyl]-N'-(3-bromophenyl)urea The title compound was prepared using the procedures described in Examples 9D and 9E except using 1-bromo-3-isocyanatobenzene instead of 1-fluoro-2-isocyanato-4-trifluoromethylbenzene in Example 9D. $^1$H NMR (300 MHz, DMSO-D$_6$) δ ppm 3.13-3.24 (m, 2H), 3.48-3.59 (m, 2H), 7.13-7.37 (m, 3H), 7.55 (d, J=8.81 Hz, 2H), 7.78 (s, 2H), 7.87 (t, J=2.03 Hz, 1H), 8.04 (d, J=8.82 Hz, 2H), 8.08 (s, 1H), 8.44-8.64 (m, J=2.03 Hz, 1H), 9.16 (s, 1H), 9.25 (s, 1H). MS(ESI(+)) m/e 454 (M+H)+.

EXAMPLE 16

N-[4-(4-amino-8,9-dihydro-7H-pyrimido[4,5-b][1,4]diazepin-6-yl)phenyl]-N'-[4-(trifluoromethyl)phenyl]urea The title compound was prepared using the procedures described in Examples 9D and 9E except using 1-isocyanato-4-trifluoromethylbenzene instead of 1-fluoro-2-isocyanato-4-trifluoromethylbenzene in Example 9D. $^1$H NMR (300 MHz, DMSO-D$_6$) δ ppm 3.14-3.25 (m, 2H), 3.49-3.59 (m, 2H), 7.56 (d, J=8.81 Hz, 2H), 7.61-7.71 (m, 4H), 7.75 (s, 2H), 8.04 (d, J=8.81 Hz, 2H), 8.08 (s, 1H), 8.52 (s, 1H), 9.29 (s, 1H), 9.37 (s, 1H). MS(ESI(+)) m/e 442 (M+H)+.

EXAMPLE 17

N-[4-(4-amino-8,9-dihydro-7H-pyrimido[4,5-b][1,4]diazepin-6-yl)phenyl]-N'-[2-fluoro-3-(trifluoromethyl)phenyl]urea The title compound was prepared using the procedures described in Examples 9D and 9E except using 1-fluoro-2-isocyanato-6-trifluoromethylbenzene instead of 1-fluoro-2-isocyanato-4-trifluoromethylbenzene in Example 9D. $^1$H NMR (300 MHz, DMSO-D$_6$) δ ppm 3.03-3.14 (m, 2H), 3.35-3.47 (m, 2H), 6.45 (s, 2H), 7.12 (t, J=4.07 Hz, 1H), 7.31-7.43 (m, 2H), 7.52 (d, J=8.82 Hz, 2H), 7.68 (s, 1H), 7.95 (d, J=8.82 Hz, 2H), 8.38-8.53 (m, 1H), 8.85 (d, J=2.71 Hz, 1H), 9.33 (s, 1H). MS(ESI(+)) m/e 460 (M+H)+.

EXAMPLE 18

N-[4-(4-amino-8,9-dihydro-7H-pyrimido[4,5-b][1,4]diazepin-6-yl)phenyl]-3-[3-(trifluoromethyl)phenyl]acrylamide

EXAMPLE 18A

N-{4-[3-(6-Amino-5-nitro-pyrimidin-4-ylamino)propionyl]phenyl}-3-(3-trifluoromethyl-phenyl)acrylamide An ice cold solution of Example 9C (91 mg) and pyridine (27 mg) in DMF (2 mL) was treated with 3-(3-trifluoromethylphenyl)acryloyl chloride (77 mg), allowed to warm up to room temperaturem then stirred overnight. The reaction was partitioned between water and EtOAc, the organic extract was washed with brine, dried (MgSO$_4$) and concentrated to give 70 mg of the title compound, which was used as is in the following experiment. MS(ESI(+)) m/e 501 (M+H)+.

EXAMPLE 18B

N-[4-(4-amino-8,9-dihydro-7H-pyrimido[4,5-b][1,4]diazepin-6-yl)phenyl]-3-[3-(trifluoromethyl)phenyl]acrylamide The title compound was prepared using the procedure described in Example 9E except using Example 18A for Example 9D. $^1$H NMR (300 MHz, DMSO-D$_6$) δ ppm 3.03-3.15 (m, 2H), 3.38-3.50 (m, 2H), 6.48 (s, 2H), 6.98 (d, J=15.60 Hz, 1H), 7.15 (t, J=4.24 Hz, 1H), 7.58-7.91 (m, 6H), 7.86-8.15 (m, 4H), 10.42 (s, 1H). MS(ESI(+)) m/e 453 (M+H)$^+$.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula (I)

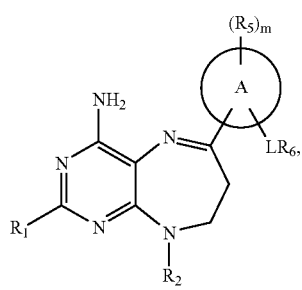

or a therapeutically acceptable salt thereof, wherein

R$_1$ is selected from the group consisting of hydrogen and NH$_2$;

R$_2$ is selected from the group consisting of hydrogen, alkoxycarbonyl, alkyl, alkylcarbonyl, arylalkoxycarbonyl, and heterocyclealkyl;

A is selected from the group consisting of phenyl and pyridinyl;

L is selected from the group consisting of —(CH$_2$)$_n$N(R$_3$)C(O)—, —N(R$_3$)C(O)(CH$_2$)$_n$—, and —(CH$_2$)$_n$N(R$_3$)C(O)N(R$_4$)—;

n is 0, 1, 2, 3, 4, 5 or 6;

R$_3$ and R$_4$ are independently selected from the group consisting of hydrogen and alkyl;

R$_5$ is independently selected from the group consisting of alkenyl, alkoxy, alkoxycarbonyl, alkyl, alkynyl, haloalkoxy, haloalkyl, halogen, hydroxy, hydroxyalkyl, and NR$_A$R$_B$;

m is 0, 1, 2, 3, or 4;

R$_6$ is selected from the group consisting of aryl, arylalkenyl, arylalkyl, cycloalkyl, cycloalkylalkenyl, cycloalkylalkyl, heteroaryl, heteroarylalkenyl, heteroarylalkyl, heterocycle, heterocyclealkenyl, and heterocyclealkyl; and R$_A$ and R$_B$ are independently selected from the group consisting of hydrogen and alkyl.

2. The compound according to claim 1 wherein

A is phenyl;

L is —(CH$_2$)$_n$N(R$_3$)C(O)N(R$_4$)—; and

R$_6$ is aryl.

3. The compound according to claim 1 wherein

R$_1$, R$_2$, R$_3$, and R$_4$ are each hydrogen;

m is 0;

A is phenyl;

L is —(CH$_2$)$_n$N(R$_3$)C(O)N(R$_4$)—;

n is 0; and

R$_6$ is aryl wherein the aryl is phenyl optionally substituted with 1 or 2 substituents selected from the group consisting of alkyl, haloalkyl, and halogen.

4. The compound according to claim 1 wherein

R$_1$, R$_2$, R$_3$, and R$_4$ are each hydrogen;

m is 1;

R$_5$ is alkyl;

A is phenyl;

L is —(CH$_2$)$_n$N(R$_3$)C(O)N(R$_4$)—;

n is 0; and

R$_6$ is aryl wherein the aryl is phenyl optionally substituted with 1 or 2 substituents selected from the group consisting of alkyl, haloalkyl, and halogen.

5. The compound according to claim 1 wherein

A is phenyl;

L is —(CH$_2$)$_n$N(R$_3$)C(O)—; and

R$_6$ is arylalkenyl.

6. The compound according to claim 1 selected from the group consisting of

N-[4-(4-amino-8,9-dihydro-7H-pyrimido[4,5-b][1,4]diazepin-6-yl)phenyl]-N'-phenylurea;

N-[3-(4-amino-8,9-dihydro-7H-pyrimido[4,5-b][1,4]diazepin-6-yl)phenyl]-N'-phenylurea;

N-[3-(4-amino-8,9-dihydro-7H-pyrimido[4,5-b][1,4]diazepin-6-yl)phenyl]-N'-[3-(trifluoromethyl)phenyl]urea;

N-[3-(4-amino-8,9-dihydro-7H-pyrimido[4,5-b][1,4]diazepin-6-yl)phenyl]-N'-(4-fluoro-3-methylphenyl)urea;

N-[4-(4-amino-8,9-dihydro-7H-pyrimido[4,5-b][1,4]diazepin-6-yl)phenyl]-N'-[3-(trifluoromethyl)phenyl]urea;

N-[4-(4-amino-8,9-dihydro-7H-pyrimido[4,5-b][1,4]diazepin-6-yl)phenyl]-N'-(2-fluoro-5-methylphenyl)urea;

N-[5-(4-amino-8,9-dihydro-7H-pyrimido[4,5-b][1,4]diazepin-6-yl)-2-methylphenyl]-N'-[3-(trifluoromethyl)phenyl]urea;

N-[5-(4-amino-8,9-dihydro-7H-pyrimido[4,5-b][1,4]diazepin-6-yl)-2-methylphenyl]-N'-(2-fluoro-5-methylphenyl)urea;

N-[4-(4-amino-8,9-dihydro-7H-pyrimido[4,5-b][1,4]diazepin-6-yl)phenyl]-N'-[2-fluoro-5-(trifluoromethyl)phenyl]urea;

N-[4-(4-amino-8,9-dihydro-7H-pyrimido[4,5-b][1,4]diazepin-6-yl)phenyl]-N'-[4-chloro-3-(trifluoromethyl)phenyl]urea;

N-[4-(4-amino-8,9-dihydro-7H-pyrimido[4,5-b][1,4]diazepin-6-yl)phenyl]-N'-(3-chlorophenyl)urea;

N-[4-(4-amino-8,9-dihydro-7H-pyrimido[4,5-b][1,4]diazepin-6-yl)phenyl]-N'-[4-fluoro-3-(trifluoromethyl)phenyl]urea;

N-[4-(4-amino-8,9-dihydro-7H-pyrimido[4,5-b][1,4]diazepin-6-yl)phenyl]-N'-(3-bromophenyl)urea;

N-[4-(4-amino-8,9-dihydro-7H-pyrimido[4,5-b][1,4]diazepin-6-yl)phenyl]-N'-[4-(trifluoromethyl)phenyl]urea;

N-[4-(4-amino-8,9-dihydro-7H-pyrimido[4,5-b][1,4]diazepin-6-yl)phenyl]-N'-[2-fluoro-3-(trifluoromethyl)phenyl]urea; and N-[4-(4-amino-8,9-dihydro-7H-pyrimido[4,5-b][1,4]diazepin-6-yl)phenyl]-3-[3-(trifluoromethyl)phenyl]acrylamide.

7. A pharmaceutical composition comprising a compound of claim 1 or a therapeutically acceptable salt thereof, in combination with a therapeutically acceptable carrier.

* * * * *